US012611116B2

(12) United States Patent
Hallbäck

(10) Patent No.: US 12,611,116 B2
(45) Date of Patent: Apr. 28, 2026

(54) ESTIMATION OF MIXED VENOUS OXYGEN SATURATION

(71) Applicant: MAQUET CRITICAL CARE AB, Solna (SE)

(72) Inventor: Magnus Hallbäck, Danderyd (SE)

(73) Assignee: MAQUET CRITICAL CARE AB, Solna (SE)

( * ) Notice: Subject to any disclaimer, the term of this patent is extended or adjusted under 35 U.S.C. 154(b) by 1022 days.

(21) Appl. No.: 17/755,957

(22) PCT Filed: Dec. 10, 2019

(86) PCT No.: PCT/SE2019/051262
§ 371 (c)(1),
(2) Date: May 12, 2022

(87) PCT Pub. No.: WO2021/118419
PCT Pub. Date: Jun. 17, 2021

(65) Prior Publication Data
US 2022/0378323 A1     Dec. 1, 2022

(51) Int. Cl.
*A61B 5/083*        (2006.01)
*A61M 16/00*       (2006.01)
(52) U.S. Cl.
CPC .......... *A61B 5/0836* (2013.01); *A61B 5/0833* (2013.01); *A61M 16/024* (2017.08); *A61M 2205/502* (2013.01)
(58) Field of Classification Search
None
See application file for complete search history.

(56) References Cited

U.S. PATENT DOCUMENTS

| | | | |
|---|---|---|---|
| 6,402,697 | B1 | 6/2002 | Calkins et al. |
| 7,135,001 | B2 | 11/2006 | Orr et al. |

(Continued)

FOREIGN PATENT DOCUMENTS

| | | |
|---|---|---|
| CN | 1245407 A | 2/2000 |
| EP | 2 799 008 A1 | 11/2014 |

(Continued)

OTHER PUBLICATIONS

Lavdaniti, Invasive and non-invasive methods for cardiac output measurement; International Journal of Caring Sciences, 1(3):112-117 Sep.-Dec. 2008 (Year: 2008).*

(Continued)

*Primary Examiner* — Jay B Shah
(74) *Attorney, Agent, or Firm* — Fay Kaplun & Marcin, LLP

(57)        ABSTRACT

A method is for continuous and noninvasive estimation of mixed venous blood saturation [SvO2] in a mechanically ventilated subject. The method includes the steps of measuring an expiratory carbon dioxide [CO2] content in expiration gas exhaled by the subject, measuring an expiratory flow or volume of expiration gas exhaled by the subject, estimating a cardiac output [CO] or an effective pulmonary blood flow [EPBF] of the subject from the measured expiratory CO2 content and the measured expiratory flow or volume using a capnodynamic Fick method, and estimating SvO2 based on the estimated CO or the EPBF of the subject.

15 Claims, 3 Drawing Sheets

(56) References Cited

U.S. PATENT DOCUMENTS

| 2003/0191373 | A1 | 10/2003 | Blike |
| 2013/0345586 | A1 | 12/2013 | Fisher et al. |
| 2017/0027451 | A1 | 2/2017 | Suarez Sipmann et al. |

FOREIGN PATENT DOCUMENTS

| WO | 91/07912 | | 6/1991 |
| WO | 2006/119546 | A1 | 11/2006 |
| WO | 2013/141766 | A1 | 9/2013 |
| WO | 2017/105304 | A1 | 6/2017 |
| WO | 2017/192076 | A1 | 11/2017 |
| WO | 2017/192077 | A1 | 11/2017 |
| WO | 2019/240634 | A1 | 12/2019 |

OTHER PUBLICATIONS

Cecchini et al. Non-invasive Estimation of Cardiac Output in Mechanically Ventilated Patients: A Prolonged Expiration Method; Annals of Biomedical Engineering, vol. 40, No. 8, Aug. 2012 pp. 1777-1789. (Year: 2012).*

* cited by examiner

ESTIMATION OF MIXED VENOUS OXYGEN SATURATION

TECHNICAL FIELD

The present disclosure relates to a method, a computer program and a system for continuous and noninvasive estimation of mixed venous oxygen saturation (SvO2) of a mechanically ventilated subject.

BACKGROUND

To provide adequate oxygen delivery in order to ensure satisfactory tissue oxygenation is a central task during mechanical ventilation of critically ill patients. Since cardiac output (CO) is one of the main determinants of oxygen delivery, major effort has been devoted to develop clinically useful technologies to assess this parameter in mechanically ventilated patients. Many of the technologies for CO assessment are associated with various limitations and even if the clinician can get reliable CO values it is still not easy to determine whether these values are adequate, insufficient or excessive. To better judge this, the CO value needs to be interpreted in relation to some other factor, e.g., tabulated normal values or plasma lactate levels.

Instead, a more intuitive way of understanding and interpreting whole body tissue oxygenation is to monitor mixed venous oxygen saturation (SvO2). SvO2 is the percentage of oxygen bound to haemoglobin in blood returning to the right side of the heart. This reflects the amount of oxygen still remaining in the blood after removal of oxygen needed by the body tissues. Consequently, changes in SvO2 reflects changes of the balance between oxygen delivery and oxygen demand of the tissues.

Today, SvO2 is measured invasively by placing a catheter for obtaining mixed venous blood samples in the pulmonary artery of the patient, a practice that is associated with a questionable risk-benefit relationship since pulmonary artery catheters (PACs), also known as Swan-Ganz catheters, are associated with significant morbidity and sometimes even mortality. Another disadvantage associated with PACs is that they only permit intermittent analysis of SvO2.

Central venous oxygen saturation (ScvO2) is sometimes used as a surrogate for SvO2. ScvO2 measurements may be obtained by a central venous catheter (CVC), such as an internal jugular or subclavian catheter, which is less invasive than a PAC. Another advantage of using ScvO2 instead of SvO2 is that there are CVCs equipped with fibre optics allowing for continuous monitoring of ScvO2. In clinical practice, it is normally assumed that ScvO2 has the same physiological meaning as SvO2, an assumption which at times is incorrect since ScvO2 does not always reflect the true mixed venous oxygen saturation, SvO2, of the patient.

A noninvasive or at least less invasive way of monitoring true SvO2 would represent a substantial advance with regard to hemodynamic monitoring during major surgery and more advanced intensive care of mechanically ventilated patients.

SUMMARY OF THE DISCLOSURE

It is an object of the disclosure to present an improved or at least alternative way of determining mixed venous blood saturation (SvO2) in a mechanically ventilated subject.

It is another object of the disclosure to present a method for determining SvO2, which eliminates or at least mitigates one or more of the above mentioned problems associated with the prior art.

In particular, it is an object of the disclosure to present a method for continuous and noninvasive determination of SvO2, which method may be readily applied at the bedside of a mechanically ventilated subject.

According to an aspect, these and other objects are achieved by a method for continuous and noninvasive estimation of SvO2 in a mechanically ventilated subject, comprising the steps of:

measuring an expiratory carbon dioxide (CO) content in expiration gas exhaled by the subject;

measuring an expiratory flow or volume of expiration gas exhaled by the subject;

estimating a cardiac output (CO) or an effective pulmonary blood flow (EPBF) of the subject from the measured expiratory CO2 content and the measured expiratory flow or volume using a capnodynamic Fick method, and estimating SvO2 based on the estimated CO or the EPBF of the subject.

By using a noninvasive capnodynamic Fick method for determining the CO or the EPBF of the ventilated subject, and estimating SvO2 from the thus obtained CO or EPBF value, a "capnodynamic SvO2" derived from mathematical modelling of exhaled CO2 kinetics can be obtained without the use of invasive pulmonary artery catheters or central venous catheters. The method hence provides a noninvasive or at least minimally invasive way of estimating SvO2.

Another advantage of the proposed method is that the capnodynamic SvO2 can be estimated continuously (i.e. on a breath-by-breath basis) as capnodynamic Fick methods for determination of CO or EPBF allow the CO or EPBF of the ventilated subject to be determined on a breath-by-breath basis.

According to an aspect, the method comprises estimating the EPBF of the subject from the measured expiratory CO2 content and the measured expiratory flow or volume using a capnodynamic Fick method, and estimating SvO2 based on the estimated EPBF.

Using EPBF instead of CO in the estimation of SvO2 is advantageous in that EPBF is associated with the pulmonary end capillary oxygen content (CcO2) which, via a pulmonary end capillary partial pressure of oxygen (PcO2), may be estimated from a known fraction of inspired oxygen (FiO2) and the alveolar gas equation. Estimating SvO2 based on CO, on the other hand, requires the arterial oxygen content (CaO2) of the ventilated subject to be determined, which in turn requires arterial oxygen saturation (SaO2) and arterial partial pressure of oxygen (PaO2) to be estimated.

The method may further comprise the steps of estimating an oxygen consumption (VO2) of the ventilated subject from a volume of CO2 eliminated by the subject through respiration (VCO2) and a respiratory quotient (RQ), and estimating SvO2 based on the estimated VO2 of the subject. VCO2 may be determined based on the expiratory CO2 content and the expiratory flow or volume measurements. RQ may be an assumed value that, e.g., may be selected based on the age, gender, weight and nutrition of the ventilated subject.

The introduction of RQ into a mathematic model of exhaled CO2 kinetics makes it possible to estimate VO2 from RQ and VCO2, which, in turn, makes it possible to calculate SvO2 from the Fick equation for oxygen balance in the lungs. VCO2 may be determined from the measured expiratory CO2 content and the measured expiratory flow or volume, e.g., using volumetric capnography. Consequently, in some embodiments, the SvO2 of the ventilated subject may be estimated from the estimated CO or EPBF using a calculated VO2 of the subject and the oxygen Fick equation.

When SvO2 is estimated based on an estimated EPBF of the subject, the proposed principles allow SvO2 to be calculated from an algorithm comprising a quotient between VCO2 and EPBF, which is advantageous in that the method becomes relatively robust against errors in the determination of VCO2. This is due to the fact that the error in VCO2 will introduce an error also in the EPBF determination, which errors will cancel out to a large extent when the SvO2 estimation is based on a quotient between VCO2 and EPBF.

The method may further comprise the steps of inserting the estimated CO or EPBF and the estimated VO2 of the subject into a Fick equation for oxygen in blood, expressing a variable relating to oxygen content per volume unit in mixed venous blood (CvO2) in said Fick equation in terms of partial pressure of oxygen in mixed venous blood (PvO2) and SvO2, and estimating SvO2 by solving the thus obtained equation with respect to SvO2. These operations allow SvO2 to be estimated from measured expiratory CO2 content and flow (or volume) in a computational friendly manner while bringing along the above mentioned advantages.

For example, SvO2 may be estimated based on the relationship $$SvO2 = ScO2 - \frac{VCO2}{C_H \cdot Hb \cdot EPBF \cdot RQ} + \frac{\alpha}{C_H \cdot Hb}(PcO2 - PvO2)$$

where ScO2 is the pulmonary end capillary oxygen saturation (fraction), $VCO_2$ is the CO2 elimination (ml $min^{-1}$), $C_H$ is the Hüfner constant (ml $g^{-1}$), Hb is the haemoglobin content in blood (g $l^{-1}$), EPBF is the effective pulmonary blood flow (l $min^{-1}$), RQ is the respiratory quotient, $\alpha$ is the solubility constant for O2 in blood plasma (ml $l^{-1}$ $kPa^{-1}$), PcO2 is pulmonary end capillary partial pressure of oxygen (kPa), and PvO2 is mixed venous partial pressure of oxygen (kPa).

In order to facilitate estimation of CO or EPBF of the ventilated subject using a capnodynamic Fick method, the method may further comprise the steps of ventilating the subject during an analysed sequence of breaths using a ventilation pattern comprising at least one phase of increased ventilation and at least one phase of decreased ventilation, so as to introduce a change in a level of CO2 expired by the subject, which change can be measured and used in the estimation of CO or EPBF, as will be described in more detail below. The method may further comprise the steps of estimating, using the capnodynamic Fick method, a CO or EPBF of the subject based on expiratory CO2 content and expiratory flow or volume measurements obtained during the analysed sequence of breaths, and estimating the SvO2 of the subject based on the estimated CO or EPBF of the subject.

For instance, the method may employ a capnodynamic Fick method for CO or EPBF estimation comprising the steps of:

determining, for a plurality of breaths in the analysed sequence of breaths, a first parameter related to a fraction of alveolar CO2 ($F_ACO2$) of the subject, a second parameter related to a CO2 content of arterial blood (CaCO2) or a CO2 content of pulmonary end capillary blood (CcCO2) of the subject, and a third parameter related to the VCO2 of the subject, based on the expiratory CO2 content measurements and the expiratory flow or volume measurements obtained during the analysed sequence of breaths, and
    estimating the CO or EPBF of the subject based on a correlation between the first, second and third parameter in the analysed sequence of breaths.

The above described method is typically a computer-implemented method that is carried out through execution of a computer program operating on a computer system. Thus, according to another aspect of the present disclosure, there is provided a computer program for continuous and noninvasive estimation of SvO2 in a mechanically ventilated subject by a system comprising a gas analyser for measuring an expiratory CO2 content in expiration gas exhaled by the subject, a flow or volume sensor for measuring an expiratory flow or volume of expiration gas exhaled by the subject, and a computer. The computer program comprises computer-readable instructions which, when executed by the computer, causes the system to carry out the above described method.

The computer program may comprise computer-readable instructions for estimating SvO2 of the ventilated subject in accordance with any of the above described principles. The computer program may be stored in a non-transitory computer-readable storage medium of a computer system, e.g., in the above mentioned computer for running the computer program.

According to yet another aspect of the present disclosure there is provided a system configured to carry out the above described method for continuous and noninvasive estimation of SvO2 in a mechanically ventilated subject.

According to one aspect, the system comprises a gas analyser for measuring an expiratory CO2 content in expiration gas exhaled by the subject, a flow or volume sensor for measuring an expiratory flow or volume of expiration gas exhaled by the subject, and a computer. The computer is configured to estimate a CO or an EPBF of the subject from the measured expiratory CO2 content and the measured expiratory flow or volume using a capnodynamic Fick method, and to estimate SvO2 based on the estimated CO or the EPBF of the subject.

The computer may advantageously be configured to estimate the EPBF of the subject from the measured expiratory CO2 content and the measured expiratory flow or volume using a capnodynamic Fick method, and to estimate SvO2 based on the estimated EPBF.

The computer may further be configured to estimate VO2 from VCO2 and RQ, and to estimate SvO2 based on the estimated VO2.

The computer may further be configured to estimate SvO2 based on a quotient between VCO2 and EPBF.

The computer may further be configured to insert the estimated CO or the estimated EPBF and the estimated VO2 of the subject into a Fick equation for oxygen in blood, express a variable relating to CvO2 in said Fick equation in terms of PvO2 and SvO2, and estimate SvO2 by solving the thus obtained equation with respect to SvO2.

The computer may, in one example, be configured to estimate SvO2 based on the relationship $$SvO2 = ScO2 - \frac{VCO2}{C_H \cdot Hb \cdot EPBF \cdot RQ} + \frac{\alpha}{C_H \cdot Hb}(PcO2 - PvO2)$$

where ScO2 is the pulmonary end capillary oxygen saturation (fraction), $VCO_2$ is the CO2 elimination (ml $min^{-1}$), $C_H$ (ml $g^{-1}$) is the Hüfner constant, Hb is the haemoglobin content in blood (g l$^{-1}$), EPBF is the effective pulmonary blood flow (l min$^{-1}$), RQ is the respiratory quotient, α is the solubility constant for oxygen in blood plasma (ml l$^{-1}$ kPa$^{-1}$), PcO2 is pulmonary end capillary partial pressure of oxygen (kPa), and PvO2 is mixed venous partial pressure of oxygen (kPa).

The gas analyser and the flow or volume sensor of the system may form part of a capnograph, and preferably a capnograph configured for volumetric capnography.

The system may be a monitoring system for monitoring hemodynamic parameters, including SvO2, of the ventilated subject.

The system may comprise a display for displaying hemodynamic parameters of the subject, including the estimated SvO2, to a clinician.

The system may further comprise a breathing apparatus, such as a ventilator or an anaesthesia machine, for providing mechanical ventilation to the subject. The computer may or may not be an internal computer of the breathing apparatus. Likewise, the display for displaying the hemodynamic parameters of the subject, including the estimated SvO2, may or may not be a display of the breathing apparatus.

The breathing apparatus may be configured to ventilate the subject during an analysed sequence of breaths using a ventilation pattern comprising at least one phase of increased ventilation and at least one phase of decreased ventilation, whereby the computer may be configured to estimate the CO or EPBF of the subject from expiratory CO2 content and expiratory flow or volume measurements obtained during the analysed sequence of breaths using the capnodynamic Fick method. For example, the computer may be configured to estimate the CO or EPBF of the subject based on a correlation between a first parameter related to the F$_A$CO2 of the subject, a second parameter related to the CaCO2 or the CcCO2 of the subject, and a third parameter related to the VCO2 of the subject, which parameters may be derived from the expiratory CO2 content and expiratory flow or volume measurements obtained during the analysed sequence of breaths.

More advantageous aspects of the proposed method, computer program and system will be described in the detailed description of embodiments following hereinafter.

BRIEF DESCRIPTION OF THE DRAWINGS

Embodiments of this disclosure will become more fully understood from the detailed description provided hereinafter and the accompanying drawings which are given by way of illustration only. In the different drawings, same reference numerals correspond to the same element.

6 ventilated subject, according to another exemplary embodiment of the present disclosure.

DETAILED DESCRIPTION

Figure 1:
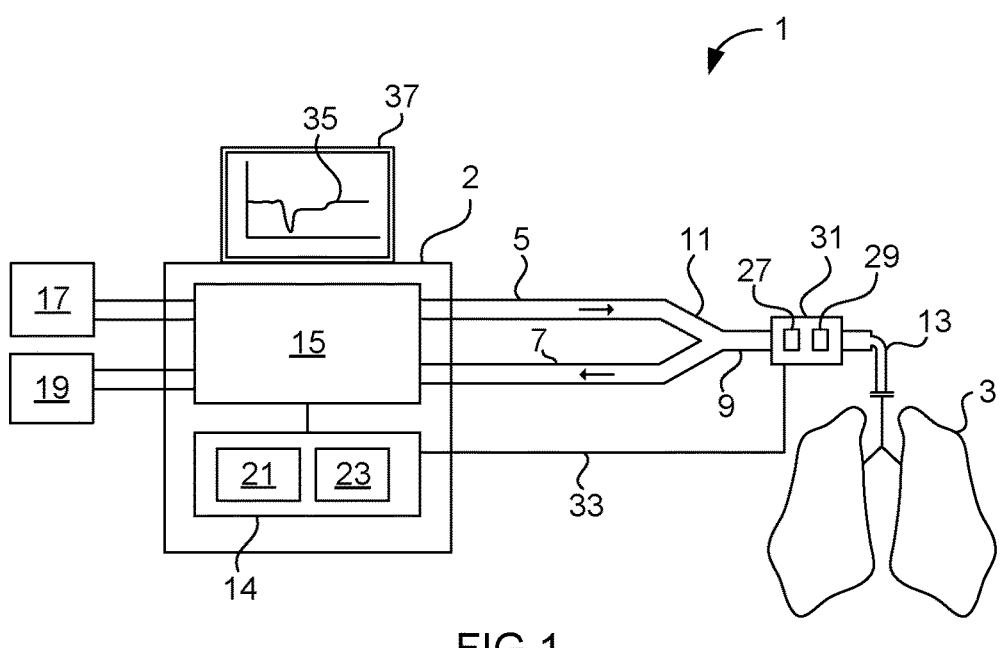
FIG. 1 illustrates a system for continuous and noninvasive estimation of SvO2 in a mechanically ventilated subject, according to an exemplary embodiment of the present disclosure.

FIG. 1 illustrates a system 1 for continuous and noninvasive estimation of mixed venous blood saturation (SvO2) in a mechanically ventilated subject 3, hereinafter referred to as the patient, according to an exemplary and non-limiting embodiment of the present disclosure.

The system 1 comprises a breathing apparatus 2, such as a ventilator or an anaesthesia machine, for providing ventilatory treatment in form of mechanical ventilation to the patient. The breathing apparatus 2 is connected to the patient via an inspiratory line 5 for supplying breathing gas to the patient 3, and an expiratory line 7 for conveying expiration gas away from the patient 3. The inspiratory line 5 and the expiratory line 7 are connected to a common line 9, via a so called Y-piece 11, which common line is connected to the patient 3 via a patient connector 13, such as a facemask or an endotracheal tube.

The system 1 further comprises a computer 14 configured to estimate the SvO2 of the ventilated patient based on a measured expiratory CO2 content and an expiratory flow or volume of expiration gas exhaled by the patient, as will be described in more detail below.

In the illustrated example, the computer 14 is an internal computer of the breathing apparatus 2, which computer also constitutes a control unit for controlling the ventilation of the patient based on preset parameters and/or measurements obtained by various sensors of the breathing apparatus. The computer 14 controls the ventilation of the patient by controlling a pneumatic unit 15 of the breathing apparatus 2, which pneumatic unit 15 is connected at one hand to one or more gas sources 17, 19 and at the other hand to the inspiratory line 5, for regulating a flow and/or pressure of breathing gas delivered to the patient 3. To this end, the pneumatic unit 15 may comprise various gas mixing and gas regulating means well known in the art of ventilation, such as gas mixing chambers, controllable gas mixing valves, one or more controllable inspiration valves and/or expiration valves, etc.

The computer 14 comprises a processor 21 and a computer-readable data storage medium 23, such as a non-transitory hardware memory device, storing a computer program for estimating SvO2 of the ventilated patient in accordance with the principles described herein. Unless stated otherwise, actions and method steps described hereinafter are performed by, or caused by, the computer 14 upon execution by the processor 21 of different code segments of the computer program stored in the data storage medium 23.

The system 1 further comprises at least one flow or volume sensor 27 for measuring a respiratory flow or volume. The respiratory flow or volume measured by the at least one flow or volume sensor includes at least an expiratory flow or volume of expiration gas exhaled by the patient. In some embodiments, the respiratory flow or volume measured by the at least one flow or volume sensor may also include an inspiratory flow or volume of breathing gas inhaled by the patient.

The system 1 also comprises at least one gas analyser 29 including a carbon dioxide (CO2) sensor for measuring a respiratory CO2 content. The CO2 content measured by the at least one gas analyser 29 is typically the CO2 content of the respiratory flow or volume measured by the at least one flow or volume sensor 27. The measured respiratory CO2 content includes at least an expiratory CO2 content in expiration gas exhaled by the patient. In some embodiments, the measured respiratory CO2 content may also include an inspiratory CO2 content inhaled by the patient during inspiration. Such an inspiratory CO2 content may result from dead-space rebreathing or rebreathing of expiration gas after removal of the majority portion of the CO2 content in the expiration gas. The respiratory CO2 content may for example be measured as a partial pressure, concentration or volume of CO2.

The at least one flow or volume sensor 27 and the at least one gas analyser 29 are operatively coupled to the computer 14 in order for the computer to estimate the SvO2 of the ventilated patient based on the respiratory flow or volume measurements and the respiratory CO2 content measurements.

In the illustrated embodiment, the flow or volume sensor 27 and the gas analyser 29 form parts of a capnograph 31 configured for volumetric capnography measurements. The capnograph 31 is arranged in the proximity of the airway opening of the patient. In this example, the capnograph 31 is arranged in the common line 9 of the breathing circuit in which it is exposed to all gas exhaled and inhaled by the patient 3. The capnograph 31 is connected to the computer 14 via a wired or wireless connection 33, and configured to communicate the result of the flow or volume and CO2 measurements to the computer 14 for further processing by the processor 21. The computer 14 may be configured to generate a volumetric capnogram 35 from the respiratory flow or volume and the respiratory CO2 content measurements received from the capnograph 31, and, optionally, to cause a display of the volumetric capnogram 35 on a display 37 of the system 1, e.g., on a display of the breathing apparatus 2.

In other alternative embodiments, the flow or volume sensor 27 and the gas analyser 29 may be located elsewhere in the breathing circuit, i.e., in other locations of the gas flow channel conveying respiration gas to and from the patient. For example, the flow or volume sensor and/or the gas analyser 29 may be incorporated into the breathing apparatus 2 and located in an expiration module of the breathing apparatus, which expiration module is connected to the expiratory line 7 for receiving the expiratory flow of expiration gas exhaled by the patient.

The computer 14 is configured to estimate the SvO2 of the ventilated patient based on an estimated cardiac output (CO) or an estimated effective (non-shunted) pulmonary blood flow (EPBF) of the patient.

The CO or EPBF of the patient is noninvasively estimated based on the respiratory flow or volume measurements and the respiratory CO2 content measurements obtained by the flow or volume sensor 27 and the gas analyser 29 using a capnodynamic method based on the Fick principle.

Capnodynamic Fick methods for estimation of CO or EPBF typically requires a level of expired CO2 to change with at least 0.2% and preferably around 0.5% or more during an analysed sequence of breaths. To this end, the computer 14 may be configured to control the breathing apparatus 2 to introduce a change in the effective ventilation of the patient by changing one or more breathing apparatus settings, which change in effective ventilation causes a desired change in the level of expired CO2 during an analysed sequence of breaths. The computer 14 may then estimate the CO or EPBF of the patient based on respiratory flow or volume measurements and respiratory CO2 content measurements obtained during said analysed sequence of breaths.

The analysed sequence of breaths may comprise any number of breaths but typically comprises 4 to 20 breaths, and preferably 4 to 12 breaths. The analysed sequence of breaths comprises at least one phase of increased ventilation and at least one phase of decreased ventilation, wherein each phase of increased ventilation and each phase of decreased ventilation comprises at least one breath, typically at least two breaths, and preferably two to six breaths. The transition from the phase of increased ventilation to the phase of decreased ventilation, and vice versa, is effectuated by the change in effective ventilation of the patient 3. The change in effective ventilation may be caused by the computer 14 in any manner known in the art, e.g., by changing the duration and/or the tidal volume of the breaths delivered to the patient by the breathing apparatus.

Preferably, in order to determine CO or EPBF continuously, i.e. on a breath-by-breath basis, the computer 14 is configured to cause the breathing apparatus 2 to ventilate the patient using a cyclic ventilation pattern comprising alternating phases of decreased and increased ventilation, wherein each phase of decreased ventilation is immediately followed by a phase on increased ventilation, and vice versa. A breath of increased ventilation is a breath that more efficiently ventilates the lungs of the patient than a breath of decreased ventilation, and vice versa. The purpose of changing the effective ventilation of the patient by providing alternating sequences of breaths of increased ventilation and breaths of decreased ventilation is thus to cause changes in the level of expired CO2, which changes can be measured and used in the determination of CO or EPBF. Preferably, but not necessarily, the number of breaths in each cycle of the cyclic ventilation pattern corresponds to the number of breaths in the analysed sequence of breaths.

The computer 14 may be configured to estimate the CO or EPBF of the ventilated patient in accordance with any known noninvasive capnodynamic Fick method, e.g., in accordance with any of the methods disclosed in WO 2006/119546, U.S. Pat. No. 7,135,001, WO 2013/141766, EP2799008, WO 2017/105304, WO 2017/192076, WO 2017/192077 or the not yet published PCT application PCT/SE2018/050606.

In an exemplary and non-limiting example, the computer 14 is configured to estimate the CO or EPBF of the patient based on the respiratory flow or volume measurements and the respiratory CO2 content measurements obtained by the flow or volume sensor 27 and the gas analyser 29 using the following capnodynamic equation for a single-chamber lung model, which describes how the fraction of alveolar carbon dioxide ($F_A CO2$) varies from one breath to another:

$$ELV \cdot (F_A CO2^n - F_A CO2^{n-1}) = EPBF \cdot \Delta t^n \cdot (CvCO2 - CcCO2^n) - VTCO2^n \qquad \text{(eq. 1)}$$

where ELV is the effective lung volume (liter) containing $CO_2$ at the end of expiration, $F_A CO2^n$ is the alveolar CO2 fraction, n is the current breath, n–1 is the previous breath, EPBF is the effective pulmonary blood flow (liter $min^{-1}$), $\Delta t^n$ is the duration of the breath, CvCO2 is the venous CO2 content (liter$_{gas}$ liter$_{blood}^{-1}$), CcCO2$^n$ is the pulmonary end capillary CO2 content (liter$_{gas}$ liter$_{blood}^{-1}$), and VTCO2$^n$ is the tidal elimination of CO2.

$F_A CO2^n$ may be measured by the gas analyser 29 while CcCO2$^n$ and VTCO2 may be directly calculated from $F_A CO2^n$, the tidal volume of breath n (VT$^n$), and a known deadspace volume, as well known in the art, leaving EPBF, CvCO2 and ELV as unknown physiological parameters to be determined.

Equation 1 is analogous to equation 1 in WO 2013/141766 disclosing a noninvasive and continuous method for simultaneous determination of ELV, cardiac output and CvCO2. The only difference between the equations is that equation 1 in WO 2013/141766 uses the quantities CaCO2 (arterial CO2 content) and cardiac output (denoted Q) whereas equation 1 above uses the quantities CcCO2 and EPBF.

The computer 14 may, for example, be configured to use the method disclosed in WO 2013/141766 to determine the parameter triplet {ELV, EPBF, CvCO2} from an analysed sequence of breaths, based on the correlation between the directly measureable or derivable parameters $\Delta F_A CO2$ ($=F_A CO2^n - F_A CO2^{n-1}$), CcCO2 and VTCO2 in said analysed sequence of breaths. Likewise, the computer 14 may be configured to use the method disclosed in WO 2013/141766 to determine the parameter triplet {ELV, cardiac output, CvCO2} from an analysed sequence of breaths, based on the correlation between the directly measureable or derivable parameters $\Delta F_A CO2$ ($=F_A CO2^n - F_A CO2^{n-1}$), CaCO2 and VTCO2 in said analysed sequence of breaths. As well known in the art, and as described in more detail in WO 2013/141766, CaCO2 may be derived from the measured $F_A CO2$ and a CO2 dissociation curve function for the solubility of carbon dioxide in arterial blood.

Estimation of EPBF using the method disclosed in WO 2013/141766 may involve the following mathematical operations.

Rearranging equation 1 such that the unknown parameters are gathered on the left-hand side of the equation:

$$ELV \cdot \Delta F_A CO_2{}^n - EPBF \cdot CvCO_2 \cdot \Delta t^n + EPBF \cdot CcCO_2{}^n \cdot \Delta t^n = -VTCO_2{}^n \qquad \text{(eq. 2)}$$

Writing this equation in matrix form for the breaths n=1, 2, . . . , N in the analysed sequence of breaths:

$$\begin{bmatrix} \Delta F_A CO_2^1 & -\Delta t^1 & CcCO_2^1 \cdot \Delta t^1 \\ \vdots & \vdots & \vdots \\ \Delta F_A CO_2^n & -\Delta t^n & CcCO_2^n \cdot \Delta t^n \\ \vdots & \vdots & \vdots \\ \Delta F_A CO_2^N & -\Delta t^N & CcCO_2^N \cdot \Delta t^N \end{bmatrix} \cdot \begin{bmatrix} ELV \\ EPBF \cdot CvCO_2 \\ EPBF \end{bmatrix} = \begin{bmatrix} -VTCO_2^1 \\ \vdots \\ -VTCO_2^n \\ \vdots \\ -VTCO_2^N \end{bmatrix} \quad \text{(eq.3)}$$

When the analysed sequence of breaths N comprises more than three breaths (i.e when N>3), this becomes an overdetermined system of equations and the unknown parameter triplet {ELV, EPBF·CvCO2, EPBF} and hence the physiological parameters ELV, EPBF, and CvCO2 can be determined by finding an approximate solution to the overdetermined system of equation. As well known in the art, the approximate solution to an overdetermined system of equations can be calculated in different ways, e.g. using the method of least squares. The solution to the overdetermined system of equations will depend on the correlation of the parameters $\Delta F_A CO2$, CcCO2 and VTCO2 in the cycles of the analysed sequence of breaths.

This system of equations (eq. 3) may be rewritten as $A \cdot x_A = a$, where $$A = \begin{bmatrix} \Delta F_A CO_2^1 & -\Delta t^1 & CcCO_2^1 \cdot \Delta t^1 \\ \vdots & \vdots & \vdots \\ \Delta F_A CO_2^n & -\Delta t^n & CcCO_2^n \cdot \Delta t^n \\ \vdots & \vdots & \vdots \\ \Delta F_A CO_2^N & -\Delta t^N & CcCO_2^N \cdot \Delta t^N \end{bmatrix}, x_A = \begin{bmatrix} ELV \\ EPBF \cdot CvCO_2 \\ EPBF \end{bmatrix}, \text{ and } a = \begin{bmatrix} -VTCO_2^1 \\ \vdots \\ -VTCO_2^n \\ \vdots \\ -VTCO_2^N \end{bmatrix}$$

The computer 14 may for example be configured to calculate an approximate solution for the parameter triplet {ELV, EPBF·CvCO2, EBBF} by minimizing the error $|A \cdot x_A - a|$. Using the method of least squares, the solution may be calculated as:

$$x_A = (A^T \cdot A)^{-1} \cdot A^T \cdot a \qquad \text{(eq. 4)}$$

Consequently, the computer 14 may estimate the EPBF (and ELV and CvCO2) of the ventilated patient from the flow or volume and CO2 measurements obtained for an analysed sequence of breaths during which the patient is ventilated using a ventilation pattern causing the level of expired CO2 to vary during the analysed sequence of breaths. In a similar manner, as discussed above and disclosed in more detail in WO 2013/141766, the computer 14 may estimate the CO (and ELV and CvCO2) of the ventilated patient. For continuous estimation of EPBF or CO, the ventilation pattern applied to the patient by the breathing apparatus 2 should preferably be a cyclic ventilation pattern and the above calculations should be performed by the computer 14 on a breath-by-breath basis.

The thus estimated EPBF or CO of the ventilated patient is then used by the computer 14 to estimate SvO2. This is achieved by first estimating an oxygen consumption (VO2) of the patient from a volume of CO2 eliminated by the patient through respiration (VCO2) and a respiratory quotient (RQ). VO2 may then be estimated as:

$$VO2 = \frac{VCO2}{RQ} \qquad \text{(eq. 5)}$$

where VO2 is the oxygen consumption (ml min⁻¹), VCO2 is the volume of CO2 eliminated through respiration (ml min⁻¹) and RQ is the respiratory quotient.

VCO2 is determined by the computer 14 based on the respiratory flow or volume measurements and the respiratory CO2 content measurements obtained by the flow or volume sensor 27 and the gas analyser 29. In the illustrated embodiment employing a capnograph for volumetric capnography 31, VCO2 may be determined as an area under the graph of the volumetric capnogram. Typically, a mean value of VCO2 is used in the calculation. For example, VCO2 in equation 5 may be a mean value of VCO2 over 20 minutes.

RQ is a dimension less number defined as the volume of CO2 released over the volume of oxygen absorbed during respiration. RQ typically ranges between 0.7-1.0 and may be set by the computer 14 based on input patient parameters relating to, e.g., the age, gender and weight of the patient.

Once EPBF or CO and VO2 have been determined by the computer 14, SvO2 can be estimated by combining the results with the oxygen Fick equation. In the following it will be shown how to estimate SvO2 from EPBF using the oxygen Fick equation.

The oxygen Fick equation for EPBF may be written as:

$$VO2 = \frac{EPBF}{(CcO2 - CvO2)} \qquad \text{(eq. 6)}$$

where VO2 is the oxygen consumption (ml min⁻¹), EPBF is the effective (non-shunted) pulmonary blood flow (l min⁻¹), CvO2 is the mixed venous oxygen content (ml l⁻¹) and CcO2 is the pulmonary end capillary oxygen content (ml l⁻¹).

The oxygen content in pulmonary end capillary blood (CcO2) may be expressed in terms of a pulmonary end capillary partial pressure of oxygen (PcO2) and a pulmonary end capillary oxygen saturation (ScO2) as:

$$CcO2 = \alpha \cdot PcO2 + C_H \cdot Hb \cdot ScO2 \qquad \text{(eq. 7)}$$

where CcO2 is the oxygen content in pulmonary end capillary blood ($ml_{STP} \, l_{blood}^{-1}$), $\alpha = 0.224$ is the solubility constant for oxygen in blood plasma ($ml_{STP} \, l^{-1} \, kPa$), PcO2 is the pulmonary end capillary partial pressure of oxygen (kPa), $C_H = 1.35$ is the Hüfner constant ($ml_{STP} \, g^{-1}$), Hb is the haemoglobin content in blood (g l⁻¹), which may be obtained from blood sampling or any type of haemoglobin screening, and ScO2 is the pulmonary end capillary oxygen saturation (fraction). STP is the standard temperature and pressure of 0° C. and 1 atm.

Likewise, the oxygen content in mixed venous blood (CvO2) may be expressed in terms of a mixed venous partial pressure of oxygen (PvO2) and a mixed venous oxygen saturation (SvO2) as:

$$CvO2 = \alpha \cdot PvO2 + C_H \cdot Hb \cdot SvO2 \qquad \text{(eq. 8)}$$

where CvO2 is the oxygen content in mixed venous blood ($ml_{STP} \, l_{blood}^{-1}$) $\alpha = 0.224$ is the solubility constant for oxygen in blood plasma ($ml_{STP} \, l^{-1} \, kPa$), PvO2 is the mixed venous partial pressure of oxygen (kPa), $C_H = 1.35$ is the Hüfner constant ($ml_{STP} \, g^{-1}$), Hb is the haemoglobin content in blood (g l⁻¹), which may be obtained from blood sampling, and SvO2 is the mixed venous oxygen saturation (fraction).

By combining equations 5-8, SvO2 may be estimated by the computer 14 as:

$$SvO2 = ScO2 - \frac{VCO2}{C_H \cdot Hb \cdot EPBF \cdot RQ} + \frac{\alpha}{C_H \cdot Hb}(PcO2 - PvO2) \qquad \text{(eq. 9)}$$

where ScO2 is the pulmonary end capillary oxygen saturation (fraction), VCO2 is the CO2 elimination (ml min⁻¹), $C_H$ is the Hüfner constant (ml g⁻¹), Hb is the haemoglobin content in blood (g l⁻¹), EPBF is the effective pulmonary blood flow (l min⁻¹), RQ is the respiratory quotient, $\alpha$ is the solubility constant for oxygen in blood plasma (ml l⁻¹ kPa⁻¹), PcO2 is the pulmonary end capillary partial pressure of oxygen (kPa), and PvO2 is the mixed venous partial pressure of oxygen (kPa).

PcO2 can be assumed to be in equilibrium with an alveolar partial pressure of oxygen ($P_A O2$), which in turn may be estimated by the computer 14 from a set fraction of inspired oxygen (FiO2) in the breathing gas delivered to the patient, and the alveolar gas equation (see, e.g., Curran-Everett D., A classic learning opportunity from Fenn, Rahn, and Otis (1946): the alveolar gas equation. Adv Physiol Educ. 2006; 30(2):58-62).

ScO2 may be calculated by the computer 14 from PcO2 and the oxygen dissociation curve (see, e.g., Siggaard-Andersen O, Wimberley P D, Göthgen I, Siggaard-Andersen M., A mathematical model of the hemoglobin-oxygen dissociation curve of human blood and of the oxygen partial pressure as a function of temperature. Clin Chem. 1984; 30(10):1646-51). Normally, the pulmonary end capillary blood is fully saturated with oxygen, meaning that ScO2 often is close to one.

Likewise, the oxygen dissociation curve may be used by the computer 14 to determine the relation between PvO2 and SvO2, and thus to unambiguously determine an estimated value of SvO2. The relationship between PvO2 and SvO2, as specified by the oxygen dissociation curve, is nonlinear. Therefore, to solve equation 9 with regard to SvO2, the computer 14 may be configured to apply an iterative procedure for determining the relationship between PvO2 and SvO2. First, the computer may set an assumed initial value of PvO2, e.g. 5 kPa. Together with the other quantities in the right-hand-side of equation 9, a first value of SvO2 may then be calculated by the computer 14. From the thus calculated value of SvO2, a new PvO2 may be calculated using the inverse relation of the dissociation curve. This new PvO2 may be used in equation 9 to calculate a new value of SvO2, and so on. The sequence of calculations rapidly converges to a unique solution for PvO2 and SvO2, where the SvO2 value thus obtained constitutes the estimated SvO2.

In this way, a "capnodynamic SvO2" may be noninvasively estimated by the computer 14 based on respiratory CO2 and flow or volume measurements comprising at least expiratory CO2 content measurements and expiratory flow or volume measurements. Besides the noninvasive nature of the proposed procedure, the procedure is advantageous in that it provides continuous (breath-by-breath) monitoring of SvO2 since the above calculations, including the capnodynamic determination of CO or EPBF, may be performed once for each breath.

Although the above estimation of SvO2 is based on EPBF, it should be appreciated that, having regard to the teachings disclosed herein, SvO2 may, in a similar manner, be estimated from CO by substituting EPBF for CO and modifying the above equations accordingly. When doing so, equation 9 that allows SvO2 to be estimated from EPBF turns into the following equation that allows SvO2 to be estimated from CO:

$$SvO2 = SaO2 - \frac{VCO2}{C_H \cdot Hb \cdot CO \cdot RQ} + \frac{\alpha}{C_H \cdot Hb}(PcO2 - PvO2) \quad \text{(eq. 10)}$$

where SaO2 is the arterial oxygen saturation (fraction), VCO2 is the CO2 elimination (ml min$^{-1}$), $C_H$ is the Hüfner constant (ml g$^{-1}$), Hb is the haemoglobin content in blood (g l$^{-1}$), CO is the cardiac output (l min$^{-1}$), RQ is the respiratory quotient, $\alpha$ is the solubility constant for oxygen in blood plasma (ml l$^{-1}$ kPa$^{-1}$), PaO2 is the arterial partial pressure of oxygen (kPa), and PvO2 is mixed venous partial pressure of oxygen (kPa).

As well known in the art, SaO2 may be estimated from peripheral capillary oxygen concentration (SpO2), which in turn may be measured using standard techniques, such as pulse oximeter measurements. Once SaO2 is estimated, PaO2 may be estimated by determining the relationship between PaO2 and SaO2 using the oxygen dissociation curve in a procedure similar to the iterative procedure for determining SvO2 and PvO2 from the oxygen dissociation curve, described above. When SaO2 and PaO2 have been determined, said iterative procedure may be repeated for SvO2 and PvO2 to find a unique solution for SvO2 and PvO2, where the SvO2 value thus obtained constitutes the estimated SvO2.

Although, in the illustrated exemplary embodiment, the computer 14 is an internal computer of the breathing apparatus 2, it should be appreciated that the calculations for estimating SvO2 may be performed by any computer configured to receive measurements relating to a CO2 content and a flow or volume of expiration gas exhaled by the mechanically ventilated subject 3. Consequently, the computer may, for example, form part of a patient monitoring system for monitoring hemodynamic parameters of a mechanically ventilated patient. Alternatively, the computer may be a stand-alone computer, e.g., a personal computer, which is configured to receive said measurements from the breathing apparatus 2 and/or directly from the flow or volume sensor 27 and the gas analyser 29.

Figure 2:
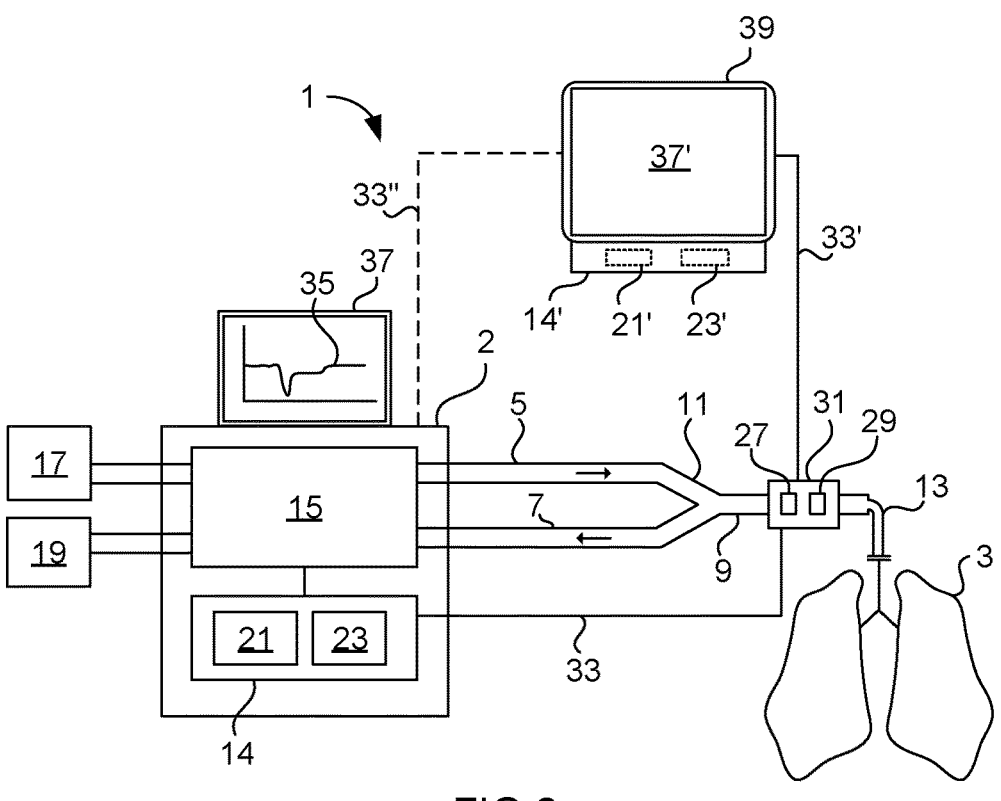
FIG. 2 illustrates a system for continuous and noninvasive estimation of SvO2 in a mechanically ventilated subject, according to another exemplary embodiment of the present disclosure.

FIG. 2 illustrates such an alternative embodiment of a system 1 for continuous and noninvasive estimation of SvO2 in a mechanically ventilated subject 3, wherein the computer 14' for estimating SvO2 based on the expiratory CO2 content and expiratory flow or volume measurements obtained by the gas analyser 29 and the flow or volume sensor 27 resides in a patient monitor 39 for monitoring hemodynamic parameters, including SvO2, of a mechanically ventilated patient 3.

The computer 14' of the patient monitor 39 may comprise a processor 21' and a computer-readable data storage medium 23', such as a non-transitory hardware memory device, storing the above mentioned computer program for estimating SvO2 of the ventilated patient in accordance with the principles described herein. The patient monitor 39 further comprises a display 37' for displaying the hemodynamic parameters, including SvO2, to a clinician.

In the illustrated embodiment, the patient monitor 39 is configured to receive the expiratory CO2 content and expiratory flow or volume measurements directly from the gas analyser 29 and the flow or volume sensor 27. The patient monitor 39 may be connected to the gas analyser 29 and the flow or volume sensor 27 via a wired or wireless connection, illustrated by the line 33' in FIG. 2. Alternatively or in addition, the patient monitor 39 may be connected to the breathing apparatus 2 and configured to receive the expiratory CO2 content and expiratory flow or volume measurements obtained by the gas analyser 29 and the flow or volume sensor 27 from the breathing apparatus 2. Such an optional wired or wireless connection between the patient monitor 39 and the breathing apparatus 2, which connection may exist instead of, or in addition to, the wired or wireless connection 33', is illustrated by the dashed line denoted 33".

Once the capnodynamic SvO2 of the ventilated patient has been estimated, the computer 14, 14' may be configured to cause display of the estimated SvO2 value to a clinician on any or both of the displays 37 and 37'. The displayed SvO2 value may serve as an indicator of adequate oxygen delivery by the breathing apparatus 2. If the SvO2 value is low, e.g., if it falls below a certain threshold value, the clinician may take appropriate action to increase oxygen delivery by the breathing apparatus and/or to improve oxygen uptake by the ventilated patient, e.g. by performing a manoeuvre for improving the CO or the EPBF of the patient.

The system 1 may further be configured to generate an alarm signal when the estimated SvO2 falls below a predetermined threshold value, in order to alert the clinician of a potentially critical situation.

In some embodiments, the system 1 may further be configured to control the breathing apparatus 2 based on the estimated SvO2, i.e., to use the estimated SvO2 as a control parameter for controlling the breathing apparatus 2. For example, the computer 14 may be configured to control the breathing apparatus 2 to increase the fraction of oxygen (FiO2) in the breathing gas delivered to the patient 3 and/or to increase the oxygen uptake by the patient when the estimated SvO2 indicates low or decreasing oxygenation of the patient. For example, the computer 14 may be configured to cause the breathing apparatus 2 to increase FiO2 when the estimated SvO2 falls below a certain threshold value. Alternatively or in addition, the computer 14 may be configured to cause the breathing apparatus 2 to perform a manoeuvre for increasing the CO or the EPBF of the patient 3 when the estimated SvO2 falls below the threshold value. For example, the manoeuvre may involve an increase in positive end-expiratory pressure (PEEP) in order to reduce the intra-pulmonary shunt of the patient, which has the effect of increasing the EPBF/CO ratio.

In some embodiments, any or both of the computers 14 and 14' may be configured to present recommendations relating to the ventilatory treatment of the patient provided by the breathing apparatus 2, based on the estimated SvO2. For example, the computer 14, 14' may be configured to present recommended breathing apparatus settings or setting adjustments based on the estimated SvO2, such as a recommended FiO2 setting or FiO2 setting adjustment. The computer 14, 14' may also be configured to present a recommendation as to a breathing apparatus manoeuvre to be performed or initiated by a breathing apparatus operator, based on the estimated SvO2. For example, the computer 14, 14' may be configured to recommend a breathing apparatus manoeuvre involving an increase in PEEP to be performed when the estimated SvO2 falls below a threshold value.

Figure 3:
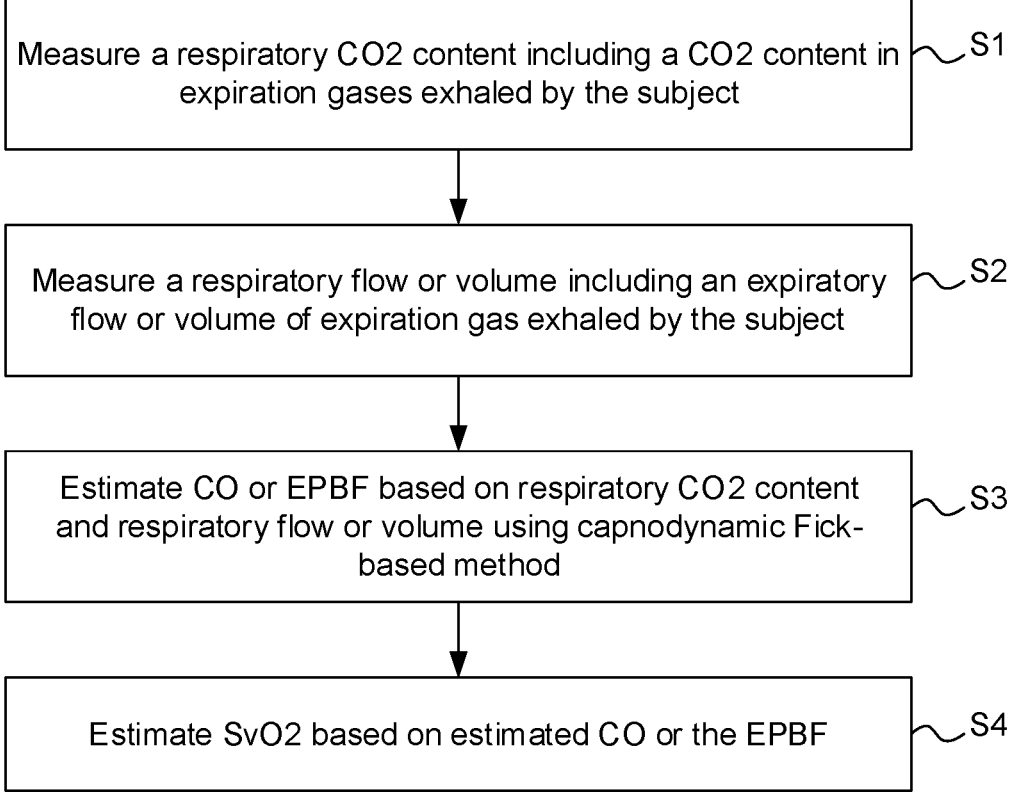
FIG. 3 is a flow chart illustrating a method for continuous and noninvasive estimation of SvO2 in a mechanically ventilated subject, according to an exemplary embodiment of the present disclosure.

FIG. 3 is a flow chart illustrating a method for continuous and noninvasive estimation of SvO2 in a mechanically ventilated subject, according to an exemplary embodiment of the present disclosure.

In a first step, S1, a respiratory CO2 content including at least an expiratory CO2 content in expiration gas exhaled by the subject is measured. The CO2 content is measured by a gas analyser including a CO2 sensor. The gas analyser may form part of a capnograph configured for volumetric capnography.

In a second step, S2, a respiratory flow or volume including at least an expiratory flow or volume of expiration gas exhaled by the subject is measured. The flow or volume is measured by a flow or volume sensor. The flow or volume sensor may form part of a capnograph configured for volumetric capnography.

In a third step, S3, the CO or the EPBF of the ventilated subject is estimated based on the measured respiratory CO2 content and the measured respiratory flow or volume using a noninvasive capnodynamic Fick method. The Fick method may be any known noninvasive Fick method for determining CO or EPBF from respiratory flow or volume and CO2 content. The CO or EPBF may be estimated by a computer upon execution of a computer program by a processor of the computer.

In a fourth and final step, S4, the SvO2 of the ventilated subject is estimated based on the CO or the EPBF estimated in step S3. This step may also be achieved by a computer upon execution of a computer program by a processor of the computer.

Figure 4:
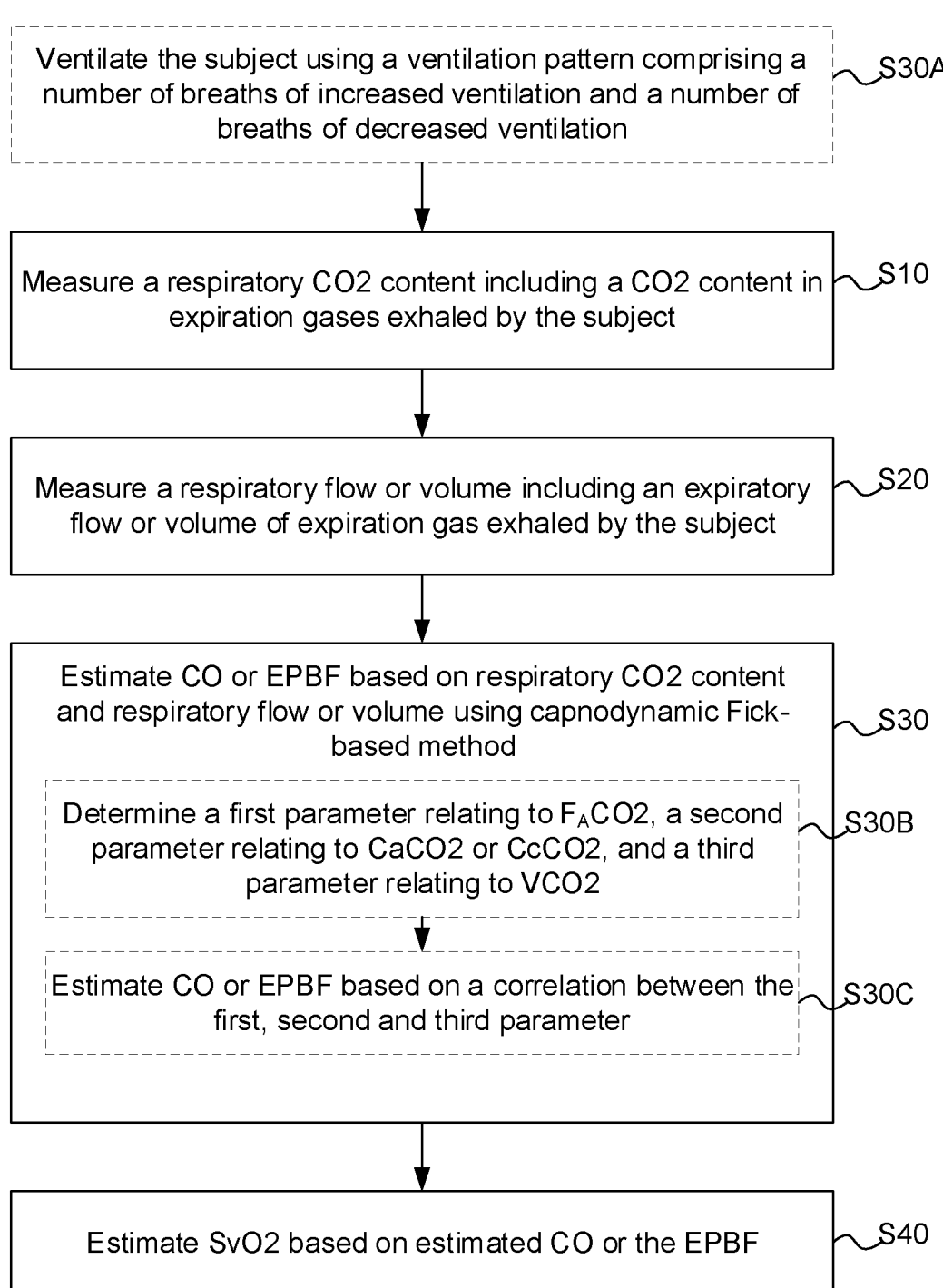
FIG. 4 is a flow chart illustrating a method for continuous and noninvasive estimation of SvO2 in a mechanically

FIG. 4 is a flow chart illustrating a method for continuous and noninvasive estimation of SvO2 in a mechanically ventilated subject, according to another exemplary embodiment of the present disclosure. Whereas the method illustrated in FIG. 3 is not limited to any particular method for estimation of CO or EPBF, the method illustrated in FIG. 4 employs the principles of the capnodynamic Fick method disclosed in WO 2013/141766.

In this exemplary embodiment, the CO or EPBF of the ventilated subject is estimated based on respiratory CO2 content and respiratory flow or volume measurements obtained during ventilation of the subject using a ventilation pattern that causes a change in the CO2 content of the expiration gas exhaled by the subject. This is achieved by controlling the breathing apparatus providing the mechanical ventilation to the subject to introduce a change in effective ventilation of the subject by ventilating the subject using a ventilation pattern comprising at least one phase of increased ventilation and at least one phase of decreased ventilation. The phase of increased ventilation comprises one or more breaths of increased ventilation and the phase of decreased ventilation comprises one or more breaths of decreased ventilation. A breath of increased ventilation is a breath that more efficiently ventilates the lungs of the patient than a breath of decreased ventilation, and vice versa. The purpose of changing the effective ventilation of the subject is thus to obtain a change in the level of expired CO2, which change can be measured and used in the determination of CO or EPBF. Therefore, in this context, a breath of decreased ventilation may also be defined as a breath that causes an increase in the level of expired CO2 compared to a breath of increased ventilation, and vice versa.

Thus, in a first step that is denoted S30A since it may be regarded as part of the estimation of the CO or EPBF of the subject taking place in a subsequent step denoted S30, the subject is ventilated using a ventilation pattern comprising a number of breaths (one or more) of decreased ventilation and a number of breaths (one or more) of increased ventilation, so as to introduce a change in a level of CO2 expired by the subject.

In a second step, S10, a respiratory CO2 content including at least an expiratory CO2 content in expiration gas exhaled by the subject is measured for an analysed sequence of breaths during which the subject is ventilated using the ventilation pattern applied to the subject in step S30A. The CO2 content is measured by a gas analyser including a CO2 sensor. The gas analyser may form part of a capnograph configured for volumetric capnography.

In a third step, S20, a respiratory flow or volume including at least an expiratory flow or volume of expiration gas exhaled by the subject is measured for the analysed sequence of breaths. The flow or volume is measured by a flow or volume sensor. The flow or volume sensor may form part of a capnograph configured for volumetric capnography.

In a fourth step, S30, the CO or the EPBF of the ventilated subject is estimated based on the respiratory CO2 content and the respiratory flow or volume measured during the analysed sequence of breath using the principles of the capnodynamic Fick method disclosed in WO 2013/141766. As described in more detail above, this means that the respiratory CO2 content and the respiratory flow or volume measurements obtained during the analysed sequence of breaths are used to derive a first parameter related to the $F_ACO2$ of the subject, a second parameter relating to any of the CaCO2 (in the determination of CO) or CcCO2 (in the determination of EPBF) of the subject, and a third parameter relating to the VCO2 of the subject (substep S30B of step S30). The CO or the EPBF of the ventilated subject is then estimated based on a correlation between the first, second and third parameter in the analysed sequence of breaths (substep S30C of step S30), e.g., using the method of least squares. These steps may all be performed by a computer upon execution of a computer program by a processor of the computer.

In a fifth and final step, S40, the SvO2 of the ventilated subject is estimated based on the CO or the EPBF estimated in step S30. This step may also be achieved by a computer upon execution of a computer program by a processor of the computer.

In FIGS. 3 and 4, steps S3 and S30 may advantageously comprise estimation of the EPBF of the ventilated subject, whereas steps S4 and S40 advantageously comprise estimation of SvO2 from the estimated EPBF using the oxygen Fick equation (Eq. 6), as described in more detail above.

As appreciated from the above description of FIGS. 1 and 2, the method may optionally comprise additional steps not indicated in any of the flowcharts illustrated in FIG. 3 or 4. For example, the method may comprise an additional step of displaying the estimated SvO2 on a display 37, 37' of the system 1, a step of presenting a recommendation relating to the ventilatory treatment of the patient provided by the breathing apparatus 2 (e.g., recommended breathing apparatus settings or adjustments), and/or a step of controlling the breathing apparatus 2 based on the estimated SvO2, e.g., a step of controlling the breathing apparatus to increase FiO2 and/or to perform an automated manoeuvre for increasing the CO or EPBF of the ventilated patient 3.

The invention claimed is:

1. A method for continuous and noninvasive estimation of mixed venous blood saturation [SvO2] in a subject mechanically ventilated via a breathing apparatus, comprising the steps of:
    measuring an expiratory carbon dioxide [CO2] content in expiration gas exhaled by the subject via a gas analyser positioned in communication with an exhalation line of the breathing apparatus;
    measuring one of an expiratory flow and a volume of expiration gas exhaled by the subject via one of a flow sensor and a volume sensor;
    estimating, via a processor of the breathing apparatus, an effective pulmonary blood flow [EPBF] of the subject from the measured expiratory CO2 content and the measured expiratory flow or volume using a capnodynamic Fick method; and
    estimating, via the processor, SvO2 based on the EPBF of the subject, wherein the SvO2 is estimated based on EPBF and not cardiac output [CO], in order for SvO2 to be estimated without determination of an arterial oxygen content [CaO2] of the subject.

2. The method of claim 1, further comprising the steps of:
    estimating an oxygen consumption [VO2] of the subject from a volume of CO2 eliminated by the subject through respiration [VCO2] and a respiratory quotient [RQ] and
    estimating SvO2 based on the estimated VO2 of the subject such that the SvO2 is estimated based on a quotient between VCO2 and EPBF.

3. The method of claim 1, further comprising the steps of:
    inserting the estimated EPBF and the estimated VO2 of the subject into a Fick equation for oxygen in blood,
    expressing a variable relating to oxygen content per volume unit in mixed venous blood [CvO2] in the Fick equation in terms of partial pressure of oxygen in mixed venous blood [PvO2] and SvO2, and
    estimating SvO2 by solving the thus obtained equation with respect to SvO2.

4. The method of claim 1, wherein SvO2 is estimated based on the relationship $$SvO2 = ScO2\frac{VCO2}{C_H \cdot Hb \cdot EPBF \cdot RQ} + \frac{\alpha}{C_H \cdot Hb}(PcO2 - PvO2)$$

where ScO2 is the pulmonary end capillary oxygen saturation (fraction), $VCO_2$ is the CO2 elimination (ml min$^{-1}$), $C_H$ is the Hüfner constant (ml g$^{-1}$), Hb is the haemoglobin content in blood (g l$^{-1}$), EPBF is the effective pulmonary blood flow (l min$^{-1}$), RQ is the

18 respiratory quotient, $\alpha$ is the solubility constant for O2 in blood plasma (ml l$^{-1}$ kPa$^{-1}$), PcO2 is pulmonary end capillary partial pressure of O2 (kPa), and PvO2 is mixed venous partial pressure of oxygen (kPa).

5. The method of claim 1, further comprising the step of:
    estimating the EPBF of the subject based on expiratory CO2 content measurements and expiratory flow or volume measurements obtained for an analysed sequence of breaths during which the subject is ventilated using a ventilation pattern comprising a number of breaths of increased ventilation and a number of breaths of decreased ventilation.

6. The method of claim 5, further comprising the steps of:
    determining, for a plurality of breaths in the analysed sequence of breaths, a first parameter related to a fraction of alveolar CO2 [$F_ACO2$] of the subject, a second parameter related to a CO2 content of arterial blood [CaCO2] or a CO2 content of pulmonary end capillary blood [CcCO2] of the subject, and a third parameter related to a CO2 elimination [VCO2] of the subject, based on the expiratory CO2 content measurements and the expiratory flow or volume measurements obtained for the analysed sequence of breaths, and
    estimating the EPBF of the subject based on a correlation between the first, second and third parameter in the analysed sequence of breaths.

7. A computer program for continuous and noninvasive estimation of mixed venous blood saturation [SvO2] in a mechanically ventilated subject using a system comprising a gas analyser measuring an expiratory CO2 content in expiration gas exhaled by the subject, a flow or volume sensor measuring an expiratory flow or volume of expiration gas exhaled by the subject, and a computer, the computer program comprises computer-readable instructions which, when executed by the computer, causes the system to carry out the method according to claim 1.

8. A system for continuous and noninvasive estimation of mixed venous blood saturation, SvO2, in a mechanically ventilated subject, comprising:
    a gas analyser positioned in communication with an exhalation line of a device providing mechanical ventilation to the subject and configured to measure an expiratory [CO2] content in expiration gas exhaled by the subject;
    a flow or volume sensor measuring an expiratory flow or volume of expiration gas exhaled by the subject; and
    a computer,
    wherein the computer is configured to:
    estimate an effective pulmonary blood flow [EPBF] of the subject from the measured expiratory CO2 content and the measured expiratory flow or volume using a capnodynamic Fick method, and
    estimate SvO2 based on the EPBF of the subject, wherein the computer is configured to estimate SvO2 based on EPBF and not cardiac output [CO], in order for SvO2 to be estimated without determination of an arterial oxygen content [CaO2] of the subject.

9. The system of claim 8, wherein the computer is configured to:
    estimate an oxygen consumption [VO2] of the subject from a volume of CO2 eliminated by the subject through respiration [VCO2] and a respiratory quotient [RQ], and
    estimate SvO2 based on the estimated VO2 of the subject, such that SvO2 is estimated based on a quotient between VCO2 and EPBF.

10. The system of claim 8, wherein the computer is configured to:

insert or the estimated EPBF and the estimated VO2 of the subject into a Fick equation for oxygen in blood, express a variable relating to oxygen content per volume unit in mixed venous blood [CvO2] in the Fick equation in terms of partial pressure of oxygen in mixed venous blood [PvO2] and SvO2, and estimate SvO2 by solving the thus obtained equation with respect to SvO2.

11. The system of claim 8, wherein the computer is configured to estimate SvO2 based on the relationship $$SvO2 = SaO2 - \frac{VCO2}{C_H \cdot Hb \cdot EPBF \cdot RQ} + \frac{\alpha}{C_H \cdot Hb}(PcO2 - PvO2)$$

where ScO2 is the pulmonary end capillary oxygen saturation (fraction), $VCO_2$ is the CO2 elimination (ml $min^{-1}$), $C_H$ is the Hüfner constant (ml $g^{-1}$), Hb is the haemoglobin content in blood (g $l^{-1}$), EPBF is the effective pulmonary blood flow (1 $min^{-1}$), RQ is the respiratory quotient, $\alpha$ is the solubility constant for oxygen in blood plasma (ml $l^{-1}$ $kPa^{-1}$), PcO2 is pulmonary end capillary partial pressure of O2 (kPa), and PvO2 is mixed venous partial pressure of oxygen (kPa).

12. The system of claim 8, further comprising:
a display,
wherein the computer is configured to cause display of the estimated SvO2 to a user on the display.

13. The system of claim 8, further comprising:
a breathing apparatus providing mechanical ventilation to the subject.

14. The system of claim 13, wherein the breathing apparatus is configured to ventilate the subject using a ventilation pattern comprising a number of breaths of increased ventilation and a number of breaths of decreased ventilation, the computer being configured to estimate the EPBF of the subject based on expiratory CO2 content measurements and expiratory flow or volume measurements obtained for an analysed sequence of breaths during which the subject is ventilated using the ventilation pattern.

15. The system of claim 14, wherein the computer is configured to determine, for a plurality of breaths in the analysed sequence of breaths, a first parameter related to a fraction of alveolar CO2 [$F_A CO2$] of the subject, a second parameter related to a CO2 content of arterial blood [$CaCO_2$] or a CO2 content of pulmonary end capillary blood [CcCO2] of the subject, and a third parameter related to a CO2 elimination [VCO2] of the subject, based on the expiratory CO2 content measurements and the expiratory flow or volume measurements, and to estimate the EPBF of the subject based on a correlation between the first, second and third parameter in the analysed sequence of breaths.

* * * * *